(12) United States Patent
Herrmann et al.

(10) Patent No.: US 9,842,237 B2
(45) Date of Patent: Dec. 12, 2017

(54) DEVICE AND METHOD FOR IDENTIFYING AN OBJECT AT LEAST PARTIALLY COVERED BY A TRANSPARENT MATERIAL

(71) Applicants: Jürgen-Peter Herrmann, Rosenheim (DE); Marius Michael Herrmann, Rosenheim (DE); Wolfgang Schorn, Hönningen (DE)

(72) Inventors: Jürgen-Peter Herrmann, Rosenheim (DE); Marius Michael Herrmann, Rosenheim (DE); Wolfgang Schorn, Hönningen (DE)

(73) Assignee: KHS GmbH, Dortmund (DE)

(*) Notice: Subject to any disclaimer, the term of this patent is extended or adjusted under 35 U.S.C. 154(b) by 0 days.

(21) Appl. No.: 15/047,825

(22) Filed: Feb. 19, 2016

(65) Prior Publication Data
US 2016/0247007 A1    Aug. 25, 2016

Related U.S. Application Data

(63) Continuation-in-part of application No. PCT/EP2014/066034, filed on Jul. 25, 2014.

(30) Foreign Application Priority Data

Aug. 20, 2013 (DE) .................. 10 2013 109 005

(51) Int. Cl.
*G06K 7/10* (2006.01)
*G01N 21/21* (2006.01)
(Continued)

(52) U.S. Cl.
CPC ......... *G06K 7/10722* (2013.01); *G01N 21/21* (2013.01); *G01N 21/84* (2013.01); *G06K 7/1413* (2013.01); *G06K 9/20* (2013.01)

(58) Field of Classification Search
CPC ... G01J 4/04; G01J 1/04; G01J 1/0425; A61B 1/00096; A61B 1/0646; G01N 21/21;
(Continued)

(56) References Cited

U.S. PATENT DOCUMENTS 5,841,538 A    11/1998 Schoeffler et al.
6,864,916 B1    3/2005 Nayar et al.
(Continued)

FOREIGN PATENT DOCUMENTS

DE            41 05 192 A1    8/1991
DE    10 2008 014 334 A1    9/2009
(Continued)

*Primary Examiner* — Thien M Le
(74) *Attorney, Agent, or Firm* — Nils H. Ljungman & Associates (57) ABSTRACT

A device and method for identifying an object at least partially covered by a transparent material. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

21 Claims, 3 Drawing Sheets

(51) Int. Cl.
   *G01N 21/84* (2006.01)
   *G06K 7/14* (2006.01)
   *G06K 9/20* (2006.01)

(58) Field of Classification Search
   CPC ..... G01N 2021/1765; G01N 2021/216; G02B 5/3025; H04N 13/0207; H04N 13/0217; H04N 1/02895; H04N 1/195
   USPC .......................................... 235/462.01–462.45
   See application file for complete search history.

(56) References Cited

U.S. PATENT DOCUMENTS

| | | | |
|---|---|---|---|
| 7,023,548 | B2 | 4/2006 | Pallingen |
| 7,253,435 | B2 | 8/2007 | Siniaguine et al. |
| 7,561,312 | B1 * | 7/2009 | Proudfoot .......... H04N 1/00013 348/370 |
| 9,317,754 | B2 * | 4/2016 | Hirai ................. G06K 9/00798 |
| 2006/0176558 | A1 * | 8/2006 | Plant ........................ G01J 1/04 359/485.02 |
| 2010/0013965 | A1 | 1/2010 | Pugh, Jr. et al. |
| 2010/0118398 | A1 * | 5/2010 | Grau ........................ G01J 4/04 359/465 |
| 2011/0038526 | A1 | 2/2011 | Czarnotta et al. |
| 2011/0050854 | A1 * | 3/2011 | Kanamori ............ G06T 7/0065 348/46 |
| 2011/0169943 | A1 | 7/2011 | Bachman, II et al. |
| 2012/0206571 | A1 * | 8/2012 | Kanamori .......... A61B 1/00096 348/45 |
| 2012/0300033 | A1 * | 11/2012 | Singh ................. A61B 1/00193 348/45 |
| 2013/0123985 | A1 * | 5/2013 | Hirai ...................... G01N 21/21 700/259 |
| 2013/0136306 | A1 | 5/2013 | Li et al. |
| 2015/0219552 | A1 * | 8/2015 | Kanamori ............. G01N 21/21 356/369 |

FOREIGN PATENT DOCUMENTS

| | | |
|---|---|---|
| DE | 20 2012 010 977 U1 | 11/2012 |
| EP | 2 618 304 A1 | 7/2013 |
| JP | H02-189 408 A | 7/1990 |
| JP | H11 175702 A | 7/1999 |
| WO | WO 2007/022985 A1 | 3/2007 |

* cited by examiner

DEVICE AND METHOD FOR IDENTIFYING AN OBJECT AT LEAST PARTIALLY COVERED BY A TRANSPARENT MATERIAL

CONTINUING APPLICATION DATA

This application is a Continuation-In-Part application of International Patent Application No. PCT/EP2014/066034, filed on Jul. 25, 2014, which claims priority from Federal Republic of Germany Patent Application No. 10 2013 109 005.2, filed on Aug. 20, 2013. International Patent Application No. PCT/EP2014/066034 was pending as of the filing date of this application. The United States was an elected state in International Patent Application No. PCT/EP2014/066034.

BACKGROUND

1. Technical Field

The present application relates to a device and method for identifying an object at least partially covered by a transparent material.

2. Background Information

Background information is for informational purposes only and does not necessarily admit that subsequently mentioned information and publications are prior art.

The present application relates to a method and device for identifying an object covered by a transparent layer at least in some sections by determining a surface property.

The method and device according to the present application may possibly be used as a deterrent to counterfeiting, smuggling, and black market sales of products, such as cartons and/or packs of cigarettes. In the European Union (EU), the illegal tobacco trade is a significant problem that costs governments billions in lost tax revenue. The taxes on cigarettes differ substantially from nation to nation in the EU and neighboring countries. For example, a pack of cigarettes in the United Kingdom may cost nine euros or more, whereas a pack of cigarettes in Ukraine may cost as little as one euro. It is therefore quite profitable for smugglers to obtain cigarettes in a lower-price country, such as Ukraine, and then sell them for a substantial profit in a higher-price country, such as the United Kingdom. Governments have tried to develop measures to counteract this illegal trade, with one such method being the tax stamp. The tax stamp identifies that the appropriate taxes for the country in which a product is being sold have been paid to that country's taxing authority. In many countries, it is a requirement that a tax stamp be affixed to a carton of cigarettes before the carton is wrapped in cellophane or similar transparent outer covering, such as a plastic. Such a system ensures that the appropriate taxes are paid at the time of manufacture and packaging of the cigarettes. In addition, the tax stamp serves as a quick identification mark so that purchasers, retailers, and government personnel can quickly identify illegal or smuggled products. However, smugglers have attempted to circumvent this system by developing counterfeit tax stamps, or by illegally obtaining a supply of legitimate tax stamps. The scheme is quite simple: cigarettes are produced in a lower-price country, then a counterfeit or fraudulent tax stamp of a higher-price country is applied to the cigarettes, and finally the cigarettes are sold in the higher-price country. To the average person, it will appear that the taxes on the cigarettes have been paid, and thus the cigarettes may be legally sold, even though no taxes were ever paid, and the profit goes to the smugglers rather than the government. It would therefore be beneficial to develop other means, in addition to or in place of tax stamp identification, to detect counterfeit or illegal cigarettes, in order to recover the lost tax revenue.

The surfaces of objects which are principally the same can be differentiated from one another by adequately precise or essentially precise or general examination. This applies in part already to the macroscopic range, but in any event in the microscopic range. In the final analysis, therefore, no two objects are completely identical.

For identifying objects, for example for examining their origin or authenticity, one could utilize a method, for example, of determining property parameters of a surface section of the object, and converting these into one or more characteristic digital values, i.e. properties of the natural surface are scanned and determined, in order from these to derive measured values which in turn correspond to digital values, which are characteristic for the surface.

The detection of the surface property may be rendered difficult, however, for example by different lighting conditions between the original determination of the parameters and at a subsequent examination procedure, since, for example, the light impinging on the surface produces reflections on the surface of the object, which are dependent on the lighting conditions. Moreover, for example, the positioning of the object at the first time that the property parameters are recorded and at a further examination may be different, with the result that different reflections are likewise caused by this, which could influence the data determined in each case.

The property parameters which are determined therefore, frequently do not correspond to the surface of the object itself, but are heavily influenced by the different surrounding surfaces. A comparison of the original data set and the data set determined for examination can therefore lead to errors in identification.

OBJECT OR OBJECTS

The present application is therefore based on an object of providing a method and device with which property parameters of a surface of an object can be determined particularly or relatively easily and reliably.

SUMMARY

The present application solves the object by a method according to the present application. Further exemplifications of the present application are also described in the present application.

A basic idea for the present application was the problem that previous surface identification methods could hitherto not be used with surfaces which are covered by a transparent layer, such as, for example, a cellophane film, since light reflections occurring on the transparent layer render a correct detection of the property parameters difficult, if not completely impossible.

The method of the present application for identifying an object covered by a transparent layer at least in some sections by determining a surface property is put into effect with an optical system which detects at least two polarization planes of light, which are reflected from the surface of the object and from the surface of the transparent layer, and, taking account of the polarization planes detected, determines the surface property in order to identify the object.

Due to the different polarization planes, it is possible for one polarization plane, in which the detected image comprises a greater number of interferences, such as light reflections, to be filtered out at the detection of the property parameters, i.e. the property parameters are detected in each possible polarization plane of the optical system, as far as possible as an image, and processed by the optical system, for example converted to a data set, and stored. During the determination, processing, or conversion, the optical system leaves the polarization planes in which the light reflections occur entirely out of consideration, or the optical system is configured in such a way that it leaves regions in polarization planes, in which undesirable light reflections have been determined, out of account in the preparation of the property parameters. It is to be noted that, in connection with this present application, the expression "surface properties" should be understood to mean the entire reflection profile of the surface, which comprises both the inherent (natural) properties, structures, material properties and roughness, as well as artificially produced properties, incurred by identification markings, embossings, structures, colors, etc. imposed or introduced.

To further explain, an image of an object or portion thereof could be first obtained under a specific set of lighting conditions. For example, the lighting in a manufacturing plant may be selected to produce a very clear and easily detectable image for high quality detection and inspection. However, once the object leaves the manufacturing plant, the object will be viewed under presumably much different lighting conditions, and thus the detected image would likely appear to be much different. For example, under such different lighting conditions, light may reflect off of the object and/or any surrounding transparent packaging or layer at one or more different angles of incidence. This is especially true in the case of transparent packaging, which may have one or more layers, and which may be altered during shipping and handling to have additional creases or folds or wrinkles that were not present at the time the original image was obtained. As a result, it may be extremely difficult to obtain a new image of a quality or clarity sufficient to enable a comparison between the new image and the original image. Light interferences, such as glare caused by specular reflection of light, may occur when trying to obtain the new image, due to the different angles at which the light approaches the object, and due to the different orientation and/or number of surfaces in the object and/or transparent material. Again, if additional wrinkling or creasing of the transparent material and/or the object occurs, additional and/or different surfaces will be present that were not previously present when the original image was obtained, and thus the new image may have areas of shine or glare that make general image detection quite difficult, and that make high quality image detection very difficult and insufficient to perform adequate image comparison.

The optical system therefore determines the property parameters of the surface of the object very largely without interfering light reflections, in one possible exemplification produced by the surface of the transparent layer.

The method of the present application therefore allows for the detection and determination exclusively of the surface properties of the object, in one possible exemplification without influences from the transparent layer arranged above it, such that it is also possible, for example, on an examination of the property parameters at a later time, at which the object no longer comprises a transparent layer, for the newly determined property parameters to be compared with the originally determined property parameters.

The optical system can be comprised of a plurality of image detection devices, for example of a plurality of image sensors, in each case with a polarization filter, wherein the polarization filters are arranged offset to one another. It is also possible, for example, for an image detection device to be arranged with a rotatable polarization filter, which for the detection of data is moved into different positions. In this situation, however, a detection of the data essentially must or should be carried out in at least two positions of the polarization filter.

According to a further exemplification of the present application, the optical system comprises a polarization sensor, i.e. an image sensor which comprises a plurality of polarization filters and which simultaneously or substantially simultaneously detects at least two or more polarization planes.

The use of some polarization filters allows for a particularly or generally rapid detection of the property parameters in several polarization planes. As a result of this, it is possible, in one possible exemplification, in an industrial use situation, for the run-through speed of the objects through the optical system to be matched to the run-through speed of the objects through an industrial device.

The surface properties determined by the optical system are, for particular preference or generally, natural surface properties, such as parameters for texture structure, roughness, color, or also for surface tension. In this situation the optical system can be configured so as to determine in common both individual property parameters as well as parameters of different properties. The "fingerprint" of the surface section which is produced by the optical system can accordingly also comprise a plurality of different parameters, as a result of which the identification precision of the object is perceptibly increased.

As already indicated heretofore, both natural and artificial properties can be detected, i.e. in principle all or substantially all or most optically detectable properties can be drawn on for the identification, such that the surface properties can also involve properties which are introduced onto or into the object. These include, for example, identification markings introduced into the surface, such as embossings, or identification markings applied onto the surface, such as characters, script characters, color markings, codes, in one possible exemplification as dot codes, barcodes, or matrix codes, and/or other artificial structures, which are intended to be used for identification, but which, under a transparent layer, cannot be adequately determined. This can also relate, for example, to surface properties which under normal light are not unambiguously or sufficiently clearly visible to the human eye, but which are visible, for example, by way of the polarization of the reflected light.

The term "transparent layer" is understood to mean all or substantially all or most layers covering a surface or a surface section of an object, which are transparent, i.e. can be seen through. This can, for example, be a transparent layer which is formed as a coating. Such a coating can be connected to the surface as fixed or detachable. These can be, for example, high-gloss coated packing papers or also lacquer coatings, for example on machine components.

According to a further exemplification of the present application, however, the transparent layer is formed as a film. The film in this situation covers at least a section of the object, which it is intended should be drawn on for the identification. It can, however, surround the object entirely. Typical are, for example, transparent films which at least partially surround the object itself or a surrounding packing, and, for example, protect it against external influences. These include, for example, cellophane films, shrink films, or transparent transport films.

The transparent layer can in principle be colored, wherein it must or should be guaranteed or essentially guaranteed or promoted that it exhibits at least a minimum of transparency. It is therefore in every case, as a minimum, capable of being seen through, such that an optical system can determine the surface arranged under the layer. In one possible exemplification, however, the transparent layer is formed as colorless, since the detection of the surface properties through a colorless transparent layer is particularly or relatively easy.

The method can in principle be used with any object of which a surface section intended for its identification is covered by a transparent layer. Accordingly, for example, machines, machine parts, consumer goods, foodstuffs, pharmaceuticals, or pharmaceutical packages, and the like, which are covered by a transparent layer at least in some sections, can be identified by means of the method according to the present application. In at least one possible exemplification, however, objects are identified with the method of the present application of which the surface comprises paper and/or plastic, in one possible exemplification a paper packing and/or plastic packing.

As discussed above, due to the high number of product falsifications, there is an increased requirement for identification with cigarettes, for example. Both cigarette packets as well as surrounding packaging of cigarette cartons are enveloped with a cellophane film in order to provide protection against moisture and dirt. This can, for example, be present on the face sides, in some sections, even as a double layer, such that a determination of the property parameters of a surface section arranged underneath the double-layer film is impossible.

By means of the method of the present application it is possible, for example before the packing of the cigarette packets into cartons, for a surface section of the surrounding packing enveloping the individual cigarette packet to be detected reliably and without influences from impinging light reflections, and, for example, to be stored in a central databank. In this situation, for example, even surface sections arranged under double-layer transparent layers and their natural or artificial surface properties can be detected. Official authorities can, for example, with cigarettes which have been definitely identified, carry out once again an identification of the properties of the surface of the surrounding packing, compare the data which is determined with the data stored in the databank, and so determine whether in fact there is a product falsification involved or, if appropriate, can trace the original delivery chain of the cigarette cartons.

In order for the property parameters originally detected by the optical system for the identification of the object to be called up at a later date at any time, the parameters which were determined are, in one possible exemplification, processed by the optical system, represented in one possible exemplification as digital values, and stored. These digital values are unique or may be unique to the surfaces concerned of the object, and at the same time represent a fingerprint of the surface, which consequently unambiguously characterizes it. In this situation, for the reliable identification, depending on the type of parameter determined, there should be a high degree of concordance between the original data and the data determined at the examination.

The optical system therefore comprises, in one possible exemplification, a data processing unit, such as, for example, a microprocessor and, if appropriate, a storage unit or a connecting unit, for example for wireless connection with a storage unit. As an alternative or supplement, the data sets can be deposited on the object itself, for example in the form of a matrix code or barcode.

In order to restrict the effort in the detection, and in one possible exemplification to limit the quantity of data detected, in most situations a defined section area of the surface is detected. The number of surface parameters determined over the section size as disclosed in the present application is particularly or generally well-suited for guaranteeing or promoting a reliable identification and restricts to a minimum the effort, in one possible exemplification of the detection, processing, and storage of the property parameters.

To further explain, the product "fingerprint" could possibly be, in many ways, as unique as human fingerprints. The optical system could detect and store multiple parameters in a portion of a product, all of which could add up to form a unique "fingerprint" for that particular product. For example, most boxes or cartons of cigarettes are made from a cellulose material, such as paper or paperboard or cardboard. To the naked eye, the surfaces of these materials appear identical. However, the cellulose fibers which make up the materials are arranged in random patterns and/or groups that render the materials anything but identical. The arrangement of the cellulose fibers could function much like the ridges and lines of a human fingerprint in identifying an individual piece or section of material. The optical system could therefore be used to detect and store an image of the cellulose fibers of a portion of box or carton of cigarettes, along with the product information. When the cartons are received in a country or made available for sale, inspection personnel could check the "fingerprint" of each carton to make sure that the cartons are eligible for sale in that country. For example, if a carton's "fingerprint" does not match any of the cartons in the database of legal cigarettes for that country, then the carton, as well as any others shipped or sold with it, are almost undoubtedly counterfeit or smuggled products. Since the arrangement of the cellulose fibers is inherent to the packaging material, it would be very difficult, if not impossible, or at least very impractical and expensive, for a counterfeiter to exactly reproduce the material. Whereas tax stamps and other indicia can be relatively easily faked using modern technology, it would not be so with cellulose fibers. In addition, if other identifying structures, such as embossments, watermarks, holograms, seals, color patterns, bar codes, etc., were also stored in conjunction with the surface characteristics of the packaging material, it would be extremely difficult, or at the least become unprofitable, for a counterfeiter to duplicate all of the structures to a level sufficient to deceive the detection system and software.

The present application further solves the object by way of a device for the identification of an object, wherein the object is covered at least in some sections by a transparent layer, and is arranged with the covered section in the detection range of an optical system, the optical system is configured so as to detect at least two polarization planes of a light reflected from the surface of the object and from the surface of the transparent layer, and taking account of the polarization planes detected, determines the surface property for the identification of the object.

The device of the present application is configured such as to detect different polarization planes of the reflected light, and to filter out the plane in which a majority of light reflections are present. This can take place, for example, in such a way that complete polarization planes or section areas of detected polarization planes, in which the optical system determines that there are light reflections, remain not taken into account in the recording or processing and preparation of a data set.

The object to be identified can in principle be any object of which the surface section to be identified is covered by a transparent layer. Accordingly, it is possible, for example, for a device of the present application to be installed permanently or substantially permanently in different devices, or for the device to be formed as a mobile unit. It may be not necessary or desired for a direct contact to pertain between the optical system and the object.

The device of the present application also makes it possible that, with a different positioning of the object upstream of the detection range of the optical system, or even with different lighting conditions at the determination of the property parameters, the device can still reliably determine the property parameters, such that the device is suitable in one possible exemplification for mobile use.

Although a number of aspects have been described in connection with a method, it is understood that these aspects also represent a description of the corresponding device. By analogy with this, aspects which have been described in connection with a device are also to be understood as a description of a corresponding method step, or as a feature of a method step.

The above-discussed exemplifications of the present invention will be described further herein below. When the word "invention" or "exemplification of the invention" is used in this specification, the word "invention" or "exemplification of the invention" includes "inventions" or "exemplifications of the invention", that is the plural of "invention" or "exemplification of the invention". By stating "invention" or "exemplification of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The present application is described in greater detail hereinafter on the basis of an exemplification.

DESCRIPTION OF EXEMPLIFICATION OR EXEMPLIFICATIONS

Figure 1:
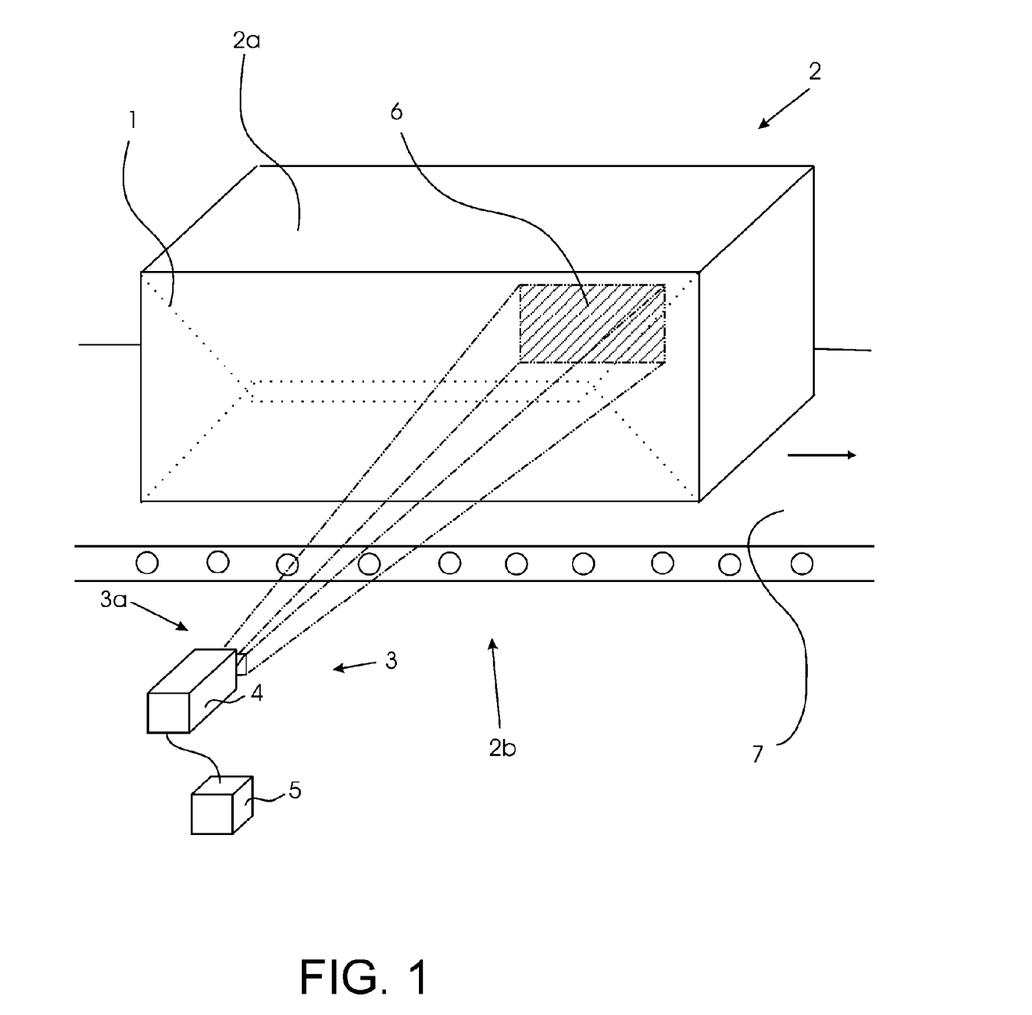
FIG. 1 shows schematically, in a perspective representation, an optical system and an object being transported on a conveyor band.

FIG. 1 shows schematically a cigarette carton 2 with an outside packing 2a, which is enveloped by a transparent layer 1 (represented here as a broken line), formed as a cellophane film or similar material. The cigarette carton 2 is being transported on a transport band 7 to a packing make-up unit (not represented here). In this situation, the cigarette carton 2 is positioned on the transport device in such a way that it points with a face side 2b towards a lens 3a of an optical system 3.

The optical system 3 comprises a polarization camera 4 or polarized camera, which is configured for taking high-resolution images. The polarization camera is connected to a data-processing and storage unit 5. The polarization camera 4 comprises a polarization sensor (not represented here), i.e. an image sensor with polarization filters, which simultaneously or essentially simultaneously or substantially simultaneously detects four different polarization planes of light.

The polarization camera 4 is therefore configured such as to detect a surface structure, in this case in one possible exemplification parameters for surface roughness, and, with the aid of the data-processing and storage unit 5 belonging to the optical system 3, to produce, from the property parameters determined, a reflection profile of the scanned surface and to convert this into a data value. As an alternative, it would also be possible, for example, for a marking applied onto the object, such as a dot code, a barcode, or a matrix code, or for an identification marking introduced into the surface, such as an embossing character, to be detected.

In operation, the polarization camera 4 is arranged aligned to the transport band in such a way that it detects an identification section 6 present beneath the transparent layer 1 (represented here as a cross-hatched surface) at the right upper corner of the cigarette carton 2.

The cigarette carton 2 is transported by means of the transport band 7 through the detection area (represented by broken lines) of the polarization camera 4. In this situation, the polarization camera 4 scans the identification section 6, i.e., it detects the light reflected from the surface of the cellophane film and the surface of the outer packing 2a of the cigarette carton 2, in four polarization planes, and conveys the information to the data-processing and storage unit 5. In this situation, due to the folding of the cellophane film, the identification section 6 is located on the face side 2b of the cigarette carton 2, in each case section by section beneath two or one layer respectively of cellophane film, as a result of which a plurality of different reflections are produced. To further explain, the transparent layer 1, that is, an outer wrap or covering made of cellophane or a plastic material, is placed around a carton 2 during manufacture. Some portions of the transparent layer 1 are formed into flaps or portions that are folded over other portions of the transparent layer 1, thereby creating a multi-layer structure. Thus, some portions of the carton 2 are covered by more than one layer of the material for the outer packing 2a. As can be seen in FIG. 1, dotted lines on the face side 2b of the carton show the flaps or folded over portions of the transparent layer 1. The identification section 6 therefore is covered in part by a double layer of transparent material, and in part by a single layer of transparent material. As discussed above, the transparent material itself and the number of layers of transparent material affect the appearance or visibility of the object disposed under or within the transparent material, such as the visual characteristics of a carton.

The polarization camera 4 detects the property parameters of the surface, determined in two or more polarization planes, and filters out the areas of the identification section 6, in which light reflections have interfered with the detection of the surface parameters of the outer packing 2a. From the filtered property parameters of the four polarization planes, the camera 4 produces a reflection profile of the detected surface section of the outer packing, and calculates, from the properties of two and more polarization planes, a reflection profile of the detected surface section of the outer packing.

The reflection profile is converted by a data processor, such as a computer or microcomputer, of the data-processing and storage unit 5 into a data set, and the stored in a data storage or memory of the data-processing and storage unit 5, such that the reflection profile can be easily called up for a later comparison with newly-determined property parameters.

Figure 2:
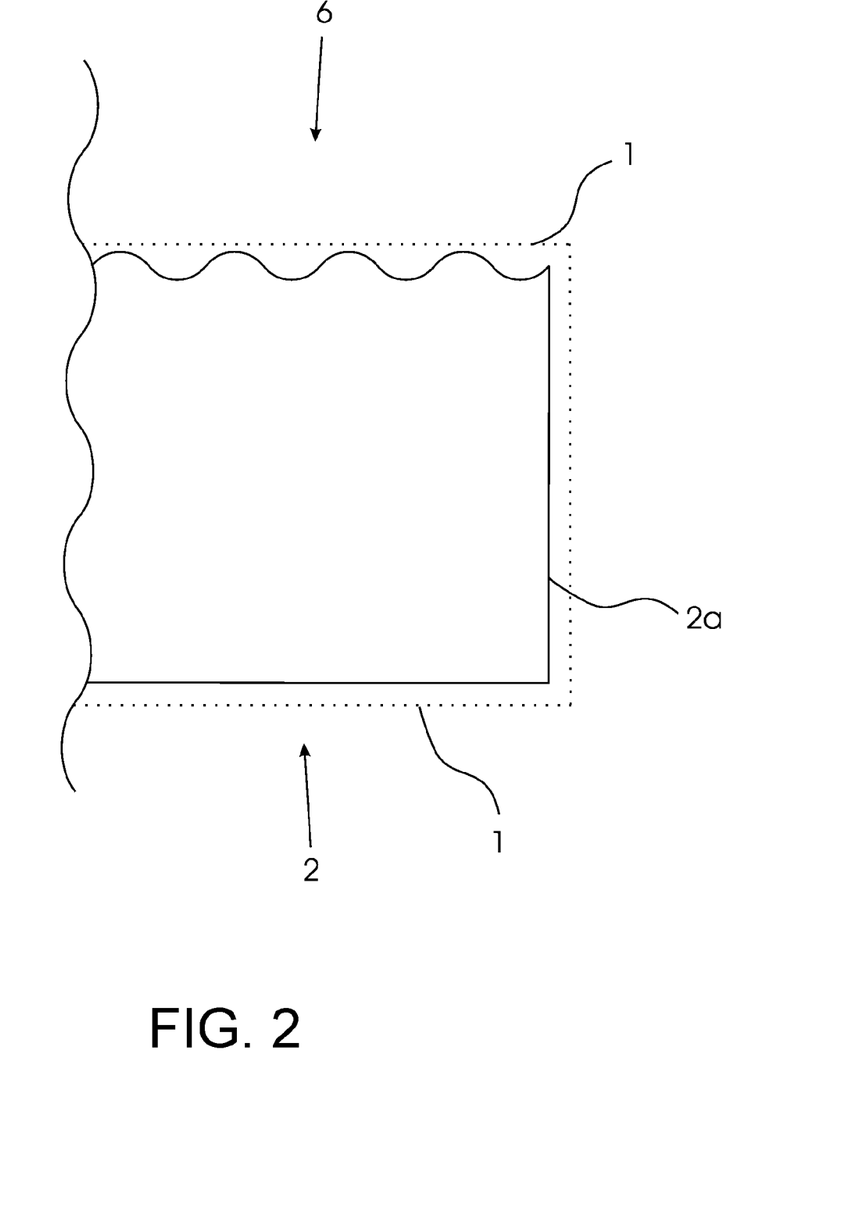
FIG. 2 shows schematically an enlarged cross-section through the surface of an identification section of the object from FIG. 2.

FIG. 2 shows schematically a cross-section through the identification section 6 of the cigarette carton 2. The cigarette carton 2 comprises the outer packing 2a, which envelopes a plurality of individual packets of cigarettes (not represented here). The outer packing 2a is made of paper. The paper exhibits individual surface properties, in this case a surface roughness (schematically represented by a corrugation shape and exaggerated for simplicity), which can be detected by the high-resolution polarization camera 4 of the optical system 3. As an alternative, a marking which has been applied, such as a code, for example, could also be detected.

Above the surface section to be detected (identification section 6), the outer packing 2a is covered by a colorless transparent cellophane film.

When light impinges onto the cigarette carton 2, the light is reflected both from the surface of the cellophane film as well as from the surface of the paper (outer packing 2a) in different polarization planes. In this situation, light reflections occur, in one possible exemplification at the surface of the cellophane film, which may prevent or restrict a precise or substantially precise detection of the surface structure of the outer packing 2a (paper).

As a result of the detection of the light reflected from the identification section 6 in different polarization planes, during the processing of the property parameters which have been determined, the optical system 3 is able to filter out the interfering light reflections, or, respectively, leave them out of consideration when producing a data set for the surface parameters determined.

Figure 3:
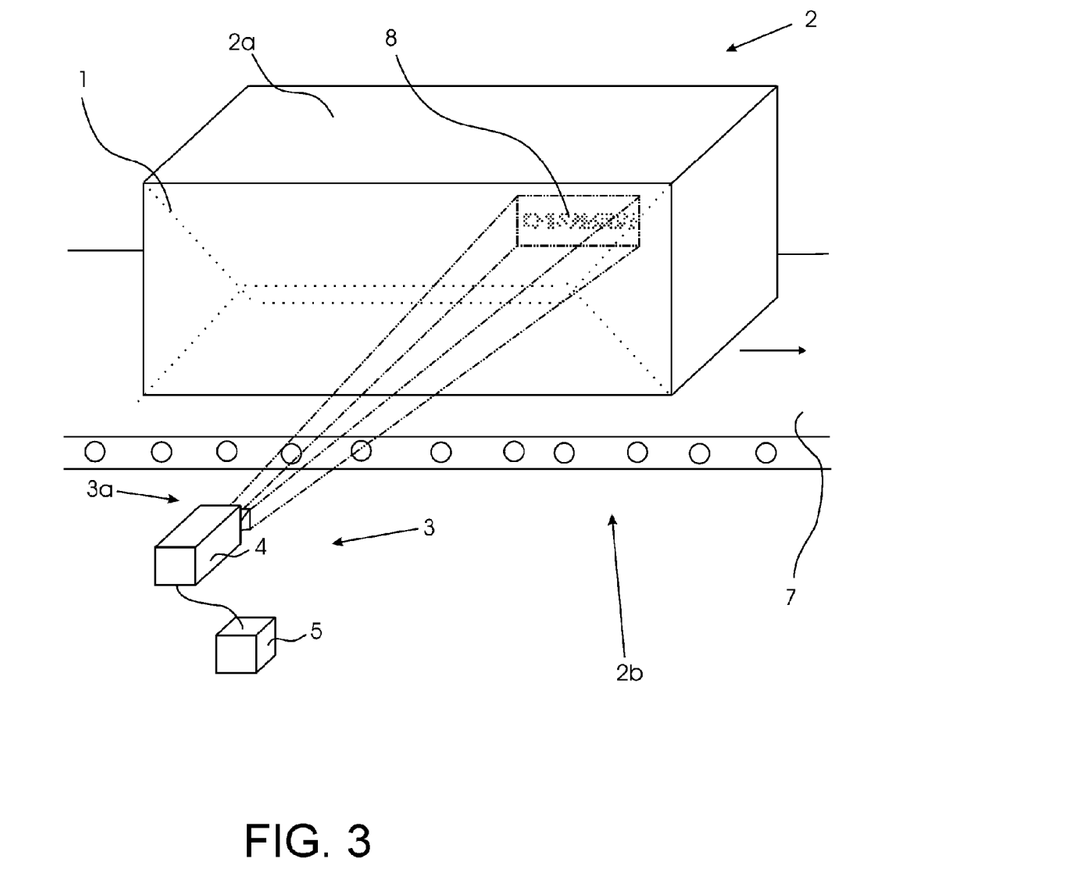
FIG. 3 shows schematically, in a perspective representation, the optical system from FIG. 1, with an object with a dot code.

FIG. 3 shows the optical system 3 and the transport band 7 from FIG. 1. On the transport band 7, a cigarette carton 2, with a dot code 8 printed on the outer packing 2a of the cigarette carton 2, is being moved past the optical system 3. The dot code 8, corresponding to the identification section 6, is covered by a cellophane film (transparent layer 1), and, due to the folding of the cellophane film, is covered in some sections by one or two layers. The determination of the dot code 8 by the optical system 3 takes place in accordance with the foregoing descriptions for FIGS. 1 and 2.

As an alternative to a dot code 8, any identification marking, applied in another manner, for example script characters, color markings, barcodes or matrix codes can also be applied and read out by the optical system 3. Other identification structures, such as embossments, seals, strips, security strips, tags, stickers, labels, holograms, and/or watermarks, could also be applied and read out by the optical system 3.

The present application relates to a method for identifying an object covered by a transparent layer at least in some sections by determining a surface property. In order to provide a method by means of which property parameters of a surface of an object, which surface is covered by a transparent layer, can be determined especially simply and reliably, an optical system according to the present application detects at least two polarization planes of light that is reflected by the surface of the object and the surface of the transparent layer and determines the surface property, while taking into account the detected polarization planes, in order to identify the object.

One feature or aspect of an exemplification is believed at the time of the filing of this patent application to possibly reside broadly in a method for identifying an object covered by a transparent layer 1 at least in some sections by determining a surface property by means of an optical system 3, wherein the optical system 3 comprises a polarization camera, which is configured for taking high-resolution images, and is connected to a data-processing and storage unit 5, and wherein the polarization camera comprises a polarization sensor, and by means of which at least two polarization planes of light, which are reflected from the surface of the object and from the surface of the transparent layer 1, are detected, and taking account of the polarization planes detected, the surface property is determined for identifying the object.

Another feature or aspect of an exemplification is believed at the time of the filing of this patent application to possibly reside broadly in the method, wherein the optical system 3 comprises an image sensor with polarization filter, which detects at least two or more polarization planes simultaneously or substantially simultaneously.

Yet another feature or aspect of an exemplification is believed at the time of the filing of this patent application to possibly reside broadly in the method, wherein, as a surface property, the texture structures, roughness, color, and/or, as a surface property, an identification marking on the surface, in one possible exemplification a dot code, matrix code, or barcode is detected.

Still another feature or aspect of an exemplification is believed at the time of the filing of this patent application to possibly reside broadly in the method, wherein the transparent layer 1 is formed as a transparent film.

A further feature or aspect of an exemplification is believed at the time of the filing of this patent application to possibly reside broadly in the method, wherein the surface of the object is of paper and/or plastic, in one possible exemplification a paper packing and/or plastic packing.

Another feature or aspect of an exemplification is believed at the time of the filing of this patent application to possibly reside broadly in the method, wherein the surface property is processed, in one possible exemplification digitalized, and stored.

Yet another feature or aspect of an exemplification is believed at the time of the filing of this patent application to possibly reside broadly in the method, wherein, for identifying the object, the property of the already determined surface section is again determined and compared with the property data first determined and stored.

One feature or aspect of an exemplification is believed at the time of the filing of this patent application to possibly reside broadly in a device for identifying an object, wherein the object is covered at least in some sections by a transparent layer 1 and is arranged with the covered section in the detection range of an optical system 3, the optical system 3 is configured so as to detect at least two polarization planes of a light reflected from the surface of the object and from the surface of the transparent layer 1, and, taking into account the detected polarization planes, to determine the surface property for identifying the object, wherein the optical system 3 comprises a polarization camera, which is also configured for taking high-resolution images, which is connected to a data-processing and storage unit 5, and wherein the polarization camera comprises a polarization sensor, by means of which four different polarization planes of light can be detected simultaneously or substantially simultaneously.

One feature or aspect of an exemplification is believed at the time of the filing of this patent application to possibly reside broadly in a method for identifying an object at least partially covered by a transparent packaging material, said method comprising the steps of: receiving, with a polarization camera, both light reflected from an outer surface of a portion of an object, and light reflected from an outer surface of at least one layer of a transparent material covering the portion of the object; detecting the reflected light in at least two polarization planes with said polarization camera; processing the reflected light using a data-processing and storage unit; and determining at least one surface property of the portion of the object using the light reflected in each of the at least two polarization planes.

Another feature or aspect of an exemplification is believed at the time of the filing of this patent application to possibly reside broadly in the method, wherein the polarization camera comprises an image sensor with polarization filter configured to detect at least two or more polarization planes simultaneously, and said step of detecting the reflected light comprises detecting at least two or more polarization planes simultaneously.

Yet another feature or aspect of an exemplification is believed at the time of the filing of this patent application to possibly reside broadly in the method, wherein the at least one surface property to be detected comprises one of or a combination of two or more of: texture structures, surface roughness, color, and an identification marking on the surface comprising at least one of a dot code, matrix code, or barcode.

Another feature or aspect of an exemplification is believed at the time of the filing of this patent application to possibly reside broadly in the method, wherein the method further comprises: repeating the steps of receiving, detecting, processing, and determining, to obtain an additional image of the at least one surface property; and comparing the additional image to the stored image to determine if the additional image is the same as the stored image, and thus determine if the object supplying the additional image is the same object that previously supplied the stored image.

Yet another feature or aspect of an exemplification is believed at the time of the filing of this patent application to possibly reside broadly in the method, wherein said method further comprises: repeating the steps of receiving, detecting, processing, and determining, to obtain an additional image of the at least one surface property; and comparing the additional image to the stored image to determine if the additional image is the same as the stored image, and thus determine if the object supplying the additional image is the same object that previously supplied the stored image.

Another feature or aspect of an exemplification is believed at the time of the filing of this patent application to possibly reside broadly in the method, wherein said step of detecting comprises detecting the reflected light in at least four polarization planes with said polarization camera.

Yet another feature or aspect of an exemplification is believed at the time of the filing of this patent application to possibly reside broadly in the method, wherein the object comprises a container containing a plurality of commercial products, and wherein the at least one surface property is configured to provide identifying information comprising at least one of: place of origin, manufacturer, manufacturing date, manufacturing location, brand, type, quantity, retail cost, and applicable taxes.

Yet another feature or aspect of an exemplification is believed at the time of the filing of this patent application to possibly reside broadly in the method, wherein said step of processing comprises digitalizing and storing the image of the at least one surface property, and wherein said method further comprises: inspecting an unverified container, the identifying information of which is unknown to the person performing or ordering the inspection, by repeating the steps of receiving, detecting, processing, and determining, to obtain an additional image of at least one surface property of the unverified container; and comparing the additional image to the stored image to determine if the additional image sufficiently matches the stored image, and thus determine if the unverified container supplying the additional image is the same container that previously supplied the stored image.

Another feature or aspect of an exemplification is believed at the time of the filing of this patent application to possibly reside broadly in the method, wherein the container is a cigarette carton containing a plurality of cigarettes or individual packs of cigarettes.

Yet another feature or aspect of an exemplification is believed at the time of the filing of this patent application to possibly reside broadly in the method, wherein said step of processing comprises digitalizing and storing the image of the at least one surface property, and wherein said method further comprises: inspecting an unverified cigarette carton, the identifying information of which is unknown to the person performing or ordering the inspection, by repeating the steps of receiving, detecting, processing, and determining, to obtain an additional image of at least one surface property of the unverified cigarette carton; and comparing the additional image to the stored image to determine if the additional image sufficiently matches the stored image, and thus determine if the unverified cigarette carton supplying the additional image is the same cigarette carton that previously supplied the stored image.

Another feature or aspect of an exemplification is believed at the time of the filing of this patent application to possibly reside broadly in the method, wherein the method further comprises: repeating the steps of receiving, detecting, processing, and determining, for each of a plurality of cigarette cartons; digitalizing and storing a plurality of images of surface properties of the cigarette cartons, which surface properties indicate that the cigarette cartons may be legally sold in a predetermined geographic area or country or nation; and thereby creating a database of images of the surface properties of the cigarette cartons.

Yet another feature or aspect of an exemplification is believed at the time of the filing of this patent application to possibly reside broadly in the method, wherein the method further comprises: inspecting a plurality of unverified cigarette cartons by repeating the steps of receiving, detecting, processing, and determining, for each of the plurality of unverified cigarette cartons, prior to sale to consumers in the predetermined geographic area or country or nation; comparing the additional images to the stored images in the database to determine if each of the additional images sufficiently matches one of the stored images in the database, and thus determining if the unverified cigarette cartons supplying the additional images are the same cigarette cartons that previously supplied the stored images; and preventing or permitting the sale of one or more of the unverified cigarette cartons, depending on whether or not each of the additional images sufficiently matches one of the stored images in the database.

Another feature or aspect of an exemplification is believed at the time of the filing of this patent application to possibly reside broadly in an optical detection arrangement, wherein said optical detection arrangement comprises: a first polarization camera and a second polarization camera, each being configured to receive both light reflected from an outer surface of a portion of a cigarette carton, and light reflected from an outer surface of at least one layer of a transparent material covering the portion of the cigarette carton, and each being configured to detect the reflected light in at least two polarization planes; said first polarization camera being disposed at a first inspection location; a data-processing and storage unit operatively connected to said first polarization camera; said data-processing and storage unit being configured to process the reflected light received by said first polarization camera, to thereby digitalize and store an image of at least one surface property of the portion of the cigarette carton, which at least one surface property provides identifying information for the cigarette carton; said second polarization camera being disposed at a second inspection location, at which second inspection location cigarette cartons are subject to an inspection performed or ordered to be performed by a person to whom identifying information of the cigarette cartons is unknown; said second polarization camera being operatively connected to said data-processing and storage unit; said data-processing and storage unit being configured to process reflected light received by said second polarization camera, to thereby digitalize an additional image of at least one surface property of a portion of an unverified cigarette carton at said second location; and said data-processing and storage unit being configured to compare the additional image to the stored image to determine if the additional image sufficiently matches the stored image, and thus determine if the unverified cigarette carton supplying the additional image is the same cigarette carton that previously supplied the stored image.

Yet another feature or aspect of an exemplification is believed at the time of the filing of this patent application to possibly reside broadly in the optical detection arrangement, wherein: said data-processing and storage unit is configured to store a plurality of images of the surface properties of portions of cigarette cartons, obtained at said first inspection location, in a database of images; and said data-processing and storage unit is configured to compare additional images, obtained at said second inspection location, to the stored images in the database to determine if each of the additional images sufficiently matches one of the stored images in the database, and thus determine if the unverified cigarette cartons supplying the additional images are the same cigarette cartons that previously supplied the stored images, to thereby prevent or permit the sale of one or more of the unverified cigarette cartons to consumers in a predetermined geographic area or country or nation.

Another feature or aspect of an exemplification is believed at the time of the filing of this patent application to possibly reside broadly in an optical detection arrangement for identifying an object at least partially covered by a transparent packaging material, said optical detection arrangement comprising: a polarization camera configured to receive both light reflected from an outer surface of a portion of an object, and light reflected from an outer surface of at least one layer of a transparent material covering the portion of the object; said polarization camera being configured to detect the reflected light in at least four polarization planes simultaneously; and a data-processing and storage unit operatively connected to said polarization camera; and said data-processing and storage unit being configured to process the reflected light, and configured to determine at least one surface property of the portion of the object using the light reflected in each of the at least four polarization planes.

The components disclosed in the patents, patent applications, patent publications, and other documents disclosed or incorporated by reference herein, may possibly be used in possible exemplifications of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one exemplification of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of polarization filters which may be used or adapted for use in at least one possible exemplification may possibly be found in DE 10 2008 014 334 A1 or DE 20 2012 010 977 U1, which are incorporated by reference herein.

Some examples of diffuse laser scattering and laser surface authentication systems and components thereof, which may be used or adapted for use in at least one possible exemplification, may possibly be found in US 2009/0283583 to Cowburn et al., and in a presentation by Mark McGlade of Ingenia Technology Ltd, published in 2006 and entitled "Laser Surface Authentication™: Natural Randomness as a Fingerprint for Product Authentication," which are incorporated by reference herein.

All, or substantially all, of the components and methods of the various exemplifications may be used with at least one exemplification or all of the exemplifications, if more than one exemplification is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible exemplification of the present application . . . " may possibly not be used or useable in any one or more exemplifications of the application.

The sentence immediately above relates to patents, patent applications, patent publications, and other documents either incorporated by reference or not incorporated by reference.

All of the patents, patent applications, patent publications, and other documents, except for the exceptions indicated herein, which were cited in the German Office Action dated Mar. 10, 2014, and/or cited elsewhere, as well as the German Office Action document itself, are hereby incorporated by reference as if set forth in their entirety herein except for the exceptions indicated herein, as follows: U.S. Pat. No. 7,253, 435 B2; U.S. Pat. No. 7,023,548 B2; U.S. Pat. No. 5,841, 538; Japanese Patent No. H02-189 048 A; and German Patent Application No 41 05 192 A1

All of the patents, patent applications, patent publications, and other documents, except for the exceptions indicated herein, which were cited in the International Search Report having a mailing date of Oct. 23, 2014, and/or cited elsewhere, as well as the International Search Report document itself, are hereby incorporated by reference as if set forth in their entirety herein except for the exceptions indicated herein, as follows: European Patent No. 2 618 304 A1; Japanese Patent No. H11 175702A; WO 2007/022985 A1, and German Patent Application No 20 2012 010977 U1.

The corresponding foreign and international patent publication applications, namely, Federal Republic of Germany Patent Application No. 10 2013 109 005.2, filed on Aug. 20, 2013, having inventors Jürgen-Peter HERRMANN, Marius Michael HERRMANN, and Wolfgang SCHORN, and 10 2013 109 005.2 and DE-PS 10 2013 109 005.2, and International Application No. PCT/EP2014/066034, filed on Jul. 25, 2014, having WIPO Publication No. WO 2015/024734 and inventors Jürgen-Peter HERRMANN, Marius Michael HERRMANN, and Wolfgang SCHORN, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2014/ 066034 and German Patent Application 10 2013 109 005.2, is solely for the purposes of providing a basis of correction of any wording in the pages of the present application, which may have been mistranslated or misinterpreted by the translator, and to provide additional information relating to technical features of one or more exemplifications, which information may not be completely disclosed in the wording in the pages of this application.

Statements made in the original foreign patent applications PCT/EP2014/066034 and DE 10 2013 109 005.2 from which this patent application claims priority which do not have to do with the correction of the translation in this patent application are not to be included in this patent application in the incorporation by reference.

Any statements about admissions of prior art in the original foreign patent applications PCT/EP2014/066034 and DE 10 2013 109 005.2 are not to be included in this patent application in the incorporation by reference, since the laws relating to prior art in non-U.S. Patent Offices and courts may be substantially different from the Patent Laws of the United States.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the exemplifications therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more exemplifications of the patents, patent applications, patent publications, and other documents, are not considered to be incorporated by reference herein for any of the patents, patent applications, patent publications, and other documents cited herein.

The description of the exemplification or exemplifications is believed, at the time of the filing of this patent application, to adequately describe the exemplification or exemplifications of this patent application. However, portions of the description of the exemplification or exemplifications may not be completely applicable to the claims as originally filed in this patent application, as amended during prosecution of this patent application, and as ultimately allowed in any patent issuing from this patent application. Therefore, any statements made relating to the exemplification or exemplifications are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the exemplification or exemplifications, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The exemplifications of the invention described herein above in the context of the preferred exemplifications are not to be taken as limiting the exemplifications of the invention to all of the provided details thereof, since modifications and variations thereof may be made without departing from the spirit and scope of the exemplifications of the invention.

What is claimed is:

1. A method for identifying an object at least partially covered by a transparent packaging material, said method comprising the steps of:
   receiving, with a polarization camera, both light reflected from an outer surface of a portion of said object, and light reflected from an outer surface of at least one layer of said transparent packaging material covering the portion of the object;
   detecting the reflected light in at least two polarization planes with said polarization camera;
   processing the reflected light using a data-processing and storage unit; and
   determining at least one surface property of the portion of the object under said transparent packaging material using the light reflected in each of the at least two polarization planes.

2. The method according to claim 1, wherein the polarization camera comprises an image sensor with polarization filter configured to detect at least two or more polarization planes simultaneously, and said step of detecting the reflected light comprises detecting at least two or more polarization planes simultaneously.

3. The method according to claim 2, wherein the at least one surface property to be detected comprises one of or a combination of two or more of:
   texture structures,
   surface roughness,
   color, and
   an identification marking on the surface comprising at least one of a dot code, matrix code, or barcode.

4. The method according to claim 3, wherein the transparent layer comprises a transparent film.

5. The method according to claim 4, wherein the surface of the object comprises paper and/or plastic, or comprises a paper packing and/or plastic packing.

6. The method according to claim 5, wherein said step of processing comprises digitalizing and storing the image of the at least one surface property.

7. The method according to claim 6, wherein said method further comprises:
   repeating the steps of receiving, detecting, processing, and determining, to obtain an additional image of the at least one surface property; and
   comparing the additional image to the stored image to determine if the additional image is the same as the stored image, and thus determine if the object supplying the additional image is the same object that previously supplied the stored image.

8. The method according to claim 7, wherein said step of detecting comprises detecting the reflected light in at least four polarization planes with said polarization camera.

9. The method according to claim 1, wherein said step of detecting comprises detecting the reflected light in at least four polarization planes with said polarization camera.

10. The method according to claim 1, wherein the object comprises a container containing a plurality of commercial products, and wherein the at least one surface property is configured to provide identifying information comprising at least one of: place of origin, manufacturer, manufacturing date, manufacturing location, brand, type, quantity, retail cost, and applicable taxes.

11. The method according to claim 10, wherein said step of processing comprises digitalizing and storing the image of the at least one surface property, and wherein said method further comprises:
   inspecting an unverified container, the identifying information of which is unknown to the person performing or ordering the inspection, by repeating the steps of receiving, detecting, processing, and determining, to obtain an additional image of at least one surface property of the unverified container; and
   comparing the additional image to the stored image to determine if the additional image sufficiently matches the stored image, and thus determine if the unverified container supplying the additional image is the same container that previously supplied the stored image.

12. The method according to claim 10, wherein the container is a cigarette carton containing a plurality of cigarettes or individual packs of cigarettes.

13. The method according to claim 12, wherein said step of processing comprises digitalizing and storing the image of the at least one surface property, and wherein said method further comprises:
   inspecting an unverified cigarette carton, the identifying information of which is unknown to the person performing or ordering the inspection, by repeating the steps of receiving, detecting, processing, and determining, to obtain an additional image of at least one surface property of the unverified cigarette carton; and comparing the additional image to the stored image to determine if the additional image sufficiently matches the stored image, and thus determine if the unverified cigarette carton supplying the additional image is the same cigarette carton that previously supplied the stored image.

14. The method according to claim 13, wherein said method further comprises:

repeating the steps of receiving, detecting, processing, and determining, for each of a plurality of cigarette cartons;

digitalizing and storing a plurality of images of surface properties of the cigarette cartons, which surface properties indicate that the cigarette cartons may be legally sold in a predetermined geographic area or country or nation; and thereby creating a database of images of the surface properties of the cigarette cartons.

15. The method according to claim 14, wherein said method further comprises:

inspecting a plurality of unverified cigarette cartons by repeating the steps of receiving, detecting, processing, and determining, for each of the plurality of unverified cigarette cartons, prior to sale to consumers in the predetermined geographic area or country or nation;

comparing the additional images to the stored images in the database to determine if each of the additional images sufficiently matches one of the stored images in the database, and thus determining if the unverified cigarette cartons supplying the additional images are the same cigarette cartons that previously supplied the stored images; and preventing or permitting the sale of one or more of the unverified cigarette cartons, depending on whether or not each of the additional images sufficiently matches one of the stored images in the database.

16. An optical detection arrangement for performing the method according to claim 13, wherein said optical detection arrangement comprises:

a first polarization camera and a second polarization camera, each being configured to receive both light reflected from an outer surface of a portion of a cigarette carton, and light reflected from an outer surface of at least one layer of a transparent material covering the portion of the cigarette carton, and each being configured to detect the reflected light in at least two polarization planes;

said first polarization camera being disposed at a first inspection location;

a data-processing and storage unit operatively connected to said first polarization camera;

said data-processing and storage unit being configured to process the reflected light received by said first polarization camera, to thereby digitalize and store an image of at least one surface property of the portion of the cigarette carton, which at least one surface property provides identifying information for the cigarette carton;

said second polarization camera being disposed at a second inspection location, at which second inspection location cigarette cartons are subject to an inspection performed or ordered to be performed by a person to whom identifying information of the cigarette cartons is unknown;

said second polarization camera being operatively connected to said data-processing and storage unit;

said data-processing and storage unit being configured to process reflected light received by said second polarization camera, to thereby digitalize an additional image of at least one surface property of a portion of an unverified cigarette carton at said second location; and said data-processing and storage unit being configured to compare the additional image to the stored image to determine if the additional image sufficiently matches the stored image, and thus determine if the unverified cigarette carton supplying the additional image is the same cigarette carton that previously supplied the stored image.

17. The optical detection arrangement for performing the method according to claim 16, wherein:

said data-processing and storage unit is configured to store a plurality of images of the surface properties of portions of cigarette cartons, obtained at said first inspection location, in a database of images; and said data-processing and storage unit is configured to compare additional images, obtained at said second inspection location, to the stored images in the database to determine if each of the additional images sufficiently matches one of the stored images in the database, and thus determine if the unverified cigarette cartons supplying the additional images are the same cigarette cartons that previously supplied the stored images, to thereby prevent or permit the sale of one or more of the unverified cigarette cartons to consumers in a predetermined geographic area or country or nation.

18. An optical detection arrangement for performing the method according to claim 1, wherein said optical detection arrangement comprises:

a polarization camera being configured to receive both light reflected from an outer surface of a portion of an object, and light reflected from an outer surface of at least one layer of a transparent material covering the portion of the object;

said polarization camera being configured to detect the reflected light in at least two polarization planes;

a data-processing and storage unit operatively connected to said polarization camera; and said data-processing and storage unit being configured to process the reflected light, and being configured to determine at least one surface property of the portion of the object using the light reflected in each of the at least two polarization planes.

19. A method for identifying an object at least partially covered by a transparent packaging material, said method comprising the steps of:

receiving, with a polarization camera, both light reflected from an outer surface of a portion of an object, and light reflected from an outer surface of at least one layer of a transparent material covering the portion of the object;

detecting the reflected light in at least two polarization planes with said polarization camera;

processing the reflected light using a data-processing and storage unit;

determining at least one surface property of the portion of the object using the light reflected in each of the at least two polarization planes;

repeating the steps of receiving, detecting, processing, and determining, to obtain an additional image of the at least one surface property; and comparing the additional image to the stored image to determine if the additional image is the same as the stored image, and thus determine if the object supplying the additional image is the same object that previously supplied the stored image.

20. An optical detection arrangement for identifying an object at least partially covered by a transparent packaging material, said optical detection arrangement comprising:
- a polarization camera configured to receive both light reflected from an outer surface of a portion of an object, and light reflected from an outer surface of at least one layer of a transparent material covering the portion of the object;
- said polarization camera being configured to detect the reflected light in at least four polarization planes simultaneously; and
- a data-processing and storage unit operatively connected to said polarization camera; and
- said data-processing and storage unit being configured to process the reflected light, and configured to determine at least one surface property of the portion of the object covered by the transparent packaging material using the light reflected in each of the at least four polarization planes.

21. An optical detection arrangement for identifying an object at least partially covered by a transparent packaging material, said optical detection arrangement comprising:
- a polarization camera configured to receive both light reflected from an outer surface of a portion of an object, and light reflected from an outer surface of at least one layer of a transparent material covering the portion of the object;
- said polarization camera being configured to detect the reflected light in at least four polarization planes simultaneously; and
- a data-processing and storage unit operatively connected to said polarization camera;
- said data-processing and storage unit being configured to process the reflected light, and configured to determine at least one surface property of the portion of the object using the light reflected in each of the at least four polarization planes; and
- said data-processing and storage unit being further configured to compare an additional image to a stored image to determine if the additional image is the same as the stored image, and thus determine if the object supplying the additional image is the same object that previously supplied the stored image.

* * * * *